(12) United States Patent
Wihren

(10) Patent No.: US 7,611,016 B2
(45) Date of Patent: Nov. 3, 2009

(54) NON-NESTING COMPONENT CARRIER TAPE

(75) Inventor: Charlie V. Wihren, Victoria, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 93 days.

(21) Appl. No.: 11/831,441

(22) Filed: Jul. 31, 2007

(65) Prior Publication Data

US 2009/0032430 A1    Feb. 5, 2009

(51) Int. Cl.
 *B65D 73/02*   (2006.01)
(52) U.S. Cl. .......................... 206/714; 206/519
(58) Field of Classification Search ................ 206/713, 206/714, 716–718, 723, 725, 518–520
See application file for complete search history.

(56) References Cited

U.S. PATENT DOCUMENTS

| 4,898,275 | A |   | 2/1990  | Skrtic          |         |
|-----------|---|---|---------|-----------------|---------|
| 5,115,911 | A | * | 5/1992  | Schulte et al.  | 206/714 |
| 5,234,104 | A | * | 8/1993  | Schulte et al.  | 206/714 |
| 5,325,654 | A |   | 7/1994  | Juntunen et al. |         |
| 5,390,472 | A |   | 2/1995  | Weiler et al.   |         |
| 5,992,639 | A |   | 11/1999 | Naito et al.    |         |
| 6,003,676 | A | * | 12/1999 | Beyer           | 206/714 |
| 6,056,124 | A | * | 5/2000  | Kaneko          | 206/714 |
| 6,105,783 | A |   | 8/2000  | Sato            |         |
| 6,216,419 | B1 | * | 4/2001 | Sakurai         | 206/714 |

FOREIGN PATENT DOCUMENTS

| JP | 06-039762   | 5/1994 |
| JP | 2000-203630 | 7/2000 |

* cited by examiner

*Primary Examiner*—Luan K Bui
(74) *Attorney, Agent, or Firm*—Melanie Gover

(57) ABSTRACT

A carrier tape for storing components and for preventing nesting of successive wraps of the carrier tape when round onto a roll. In particular, the carrier tape comprises a strip like portion defining a top surface of the tape, and wall portions defining a plurality of substantially similarly shaped pockets spaced along the carrier tape and opening through the top surface. The wall portions of the substantially similarly shaped pockets include a bottom wall portion, a first wall portion extending from the bottom wall portion to the top surface of the carrier tape, a first cross-beam wall portion extending from the bottom wall portion and located between adjacent pockets on the carrier tape, and a second cross-beam wall portion extending from the bottom wall portion and located between selected adjacent pockets on the carrier tape. One or more of the cross-beam wall portions have a notched opening formed at a selected location along a length of the first or second cross-beam wall portions.

14 Claims, 2 Drawing Sheets

NON-NESTING COMPONENT CARRIER TAPE

BACKGROUND

Carrier tape is used to transport components (e.g., electrical components such as resistors, capacitors, or integrated circuits) from a component manufacturer to a different manufacturer that assembles the components carried within the carrier tape into a complete product. The carrier tape includes a number of pockets formed within the carrier tape at regular intervals and having a geometry that is compatible with the components to be carried. The pockets are typically defined by a number of wall portions extending from a bottom portion of the pocket to a top portion of the carrier tape. In this way, the components being carried by the carrier tape rest within the defined pockets.

Typically, a carrier tape is manufactured in a first manufacturing location, wound on a reel and transported to the supplier of the components it is intended to transport. The component supplier unwinds the carrier tape from the reel, fills the pockets along the carrier tape with components, adheres a removable cover strip along the carrier tape over the component filled pockets, winds the component filled carrier tape with the attached cover strip onto a reel, and sends it to the user who feeds it from the reel onto the assembly equipment which removes the components.

A common problem associated with carrier tapes wound onto reels in this manner is the tendency for pockets on a first wrap of the carrier tape to settle or nest into the pockets of an adjacently wrapped portion of the carrier tape. The nesting of one pocket into another pocket causes the wall portions of the pockets to frictionally engage one another such that a large force is then required to unwind the carrier tape. This may result in the deforming of the carrier tape such that the automated equipment is no longer able to remove components from the carrier tape.

SUMMARY

In one aspect, the present invention is a pocket defined within a carrier tape. The pocket comprises a bottom wall portion, a first side wall portion extending from the bottom wall portion to the top surface of the carrier tape, and a second side wall portion extending from the bottom wall and having a length defined by a size of the pocket, a width defined by a distance between the pocket and an adjacently formed pocket, and a height defined by a distance between the bottom wall portion and a top surface of the second side wall portion. The second side wall portion includes a notched opening formed along a top portion of the second side wall having a length less than the length of the second side wall, a width equal to the width of the second side wall, and a height less than or equal to the height of the second side wall.

In another aspect, the present invention includes a carrier tape comprising a strip like portion defining a top surface of the carrier tape. The carrier tape includes a number of substantially similarly-shaped pockets defined by openings in the top surface of the carrier tape. One or more of the substantially similarly-shaped pockets includes a bottom wall portion, a first wall portion extending from the bottom wall portion to the top surface of the carrier tape, a first cross-beam wall portion extending from the bottom wall portion and located between adjacent pockets on the carrier tape, and a second cross-beam wall portion extending from the bottom wall portion and located between selected adjacent pockets on the carrier tape, wherein a top portion of each second cross-beam wall portion has a notched opening formed at a selected location along a length of the second cross-beam wall portion.

In another aspect of the present invention, a cover tape is adhered to at least a portion of the top surface of the carrier tape.

DETAILED DESCRIPTION

Figure 1:
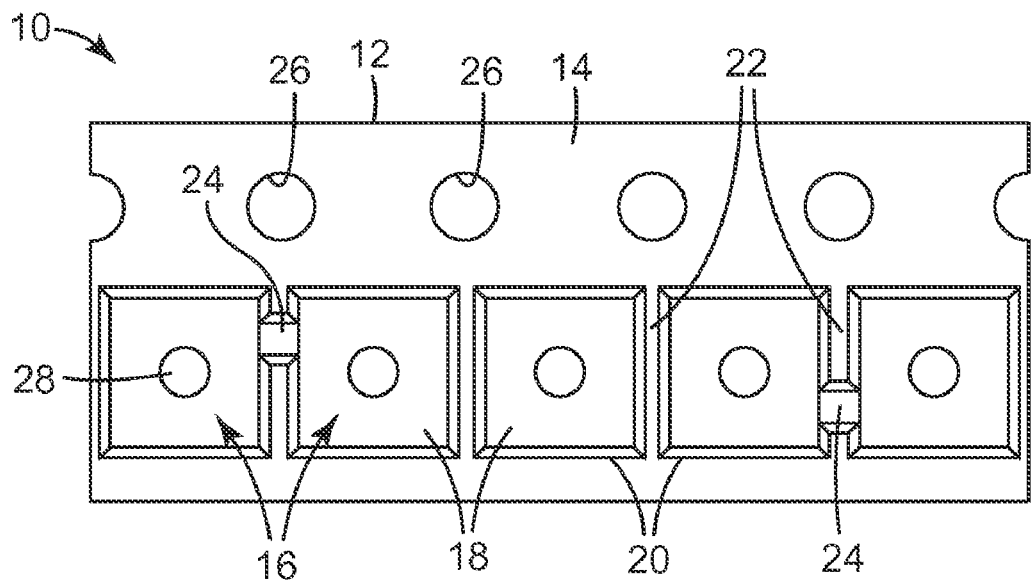
FIG. 1 is a fragmentary top view of an exemplary embodiment of a carrier tape that includes an anti-nesting feature.
Figure 2:
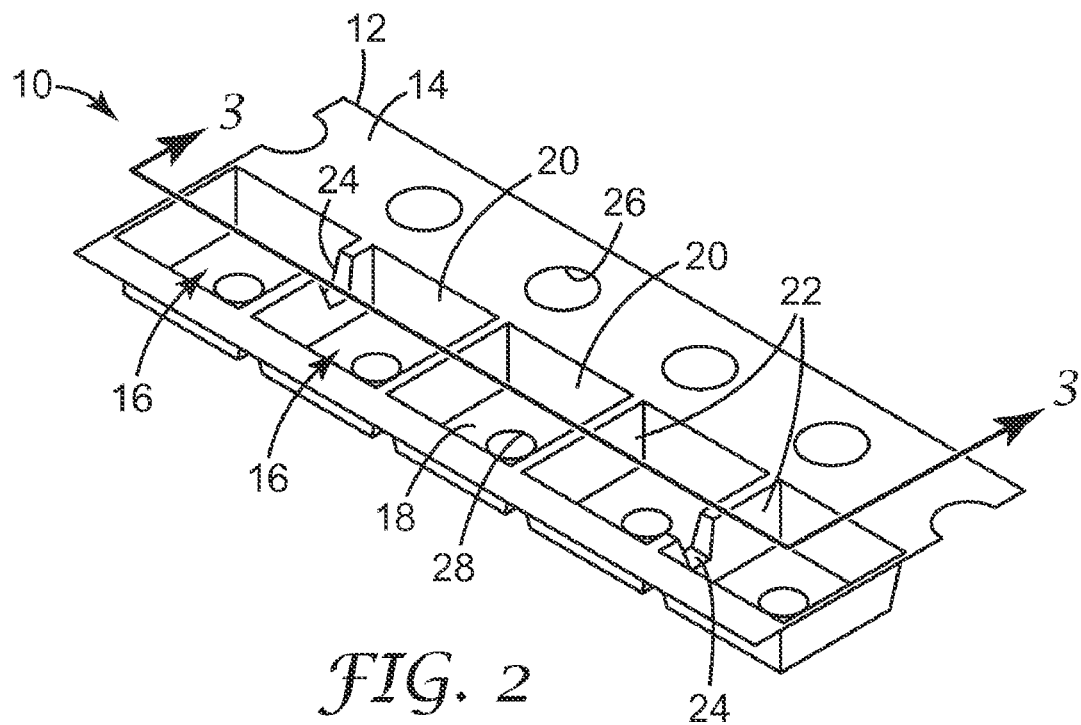
FIG. 2 is a fragmentary perspective view of the exemplary embodiment of the carrier tape shown in FIG. 1.

FIGS. 1 and 2 illustrate an exemplary embodiment of carrier tape 10 according to the present invention. FIG. 1 is a fragmentary top view of carrier tape 10, and FIG. 2 is a fragmentary perspective view of carrier tape 10. In particular, carrier tape 10 includes strip-like portion 12, top portion 14, a plurality of similarly-shaped pockets 16, bottom portion 18, side-wall portions 20, cross-beam portions 22, cross-beam notches 24, drive-sprocket openings 26, and component sensing openings 28.

Each similarly-shaped pocket 16 is defined within carrier tape 10 by a bottom portion 18, side-wall portion 20 extending from bottom portion 18 to top portion 14, and cross-beam portion 22 extending generally from bottom portion 18 toward top portion 14 and separating adjacent similarly-shaped pockets 16 from one another. One of the benefits of forming similarly-shaped pockets 16 separated by relatively narrow cross-beam portions 22 is the ability to increase the number of similarly-shaped pockets formed on carrier tape 10. However, the width of the relatively narrow cross-beam portions 22 is insufficient for forming traditional non-nesting features or structures.

In the exemplary embodiment shown in FIGS. 1 and 2, cross-beam notches 24 are defined within one or more cross-beam portions 22 to provide non-nesting functionality to carrier tape 10 within cross-beam portion 22. Cross-beam notches 24 may be formed in successive cross-beam portions 22 or may be formed on only selected cross-beam portions 22. For example, in the exemplary embodiment shown in FIG. 1, cross-beam notches 24 are formed on every third cross-beam portion 22.

In addition to selecting the cross-beam portions 22 in which to form cross-beam notches 24, the location of cross-beam notches formed along the length of a particular cross-beam portion 22 may be selectively varied. For example, in the exemplary embodiment shown in FIG. 1, a first cross-beam notch 24 formed on the left side of FIG. 1 is formed in a first position (i.e., located proximally to drive-sprocket openings 26) along the length of side-wall portion 22, and a second cross-beam notch 24 formed on the right side of FIG. 1 is formed in a second position (i.e., located distally from drive-sprocket openings 26). Likewise, the length of cross-beam notches 24 may be selectively varied depending on the application, or even within a single application. For example, in the exemplary embodiment shown in FIGS. 1 and 2, the length of cross-beam notches 24 is approximately 30% of the length of cross-beam portions 22. In other embodiments the length of cross-beam notches 24 may be selectively varied, although the length should not adversely affect the structural integrity of cross-beam portion 22. For example, extending the length of cross-beam notch 24 beyond approximately 50% of the length of cross-beam portions 22 may lead to cross-beam portions 22 bending or deforming in the region surrounding cross-beam notch 24.

In addition, the perspective view shown in FIG. 2 illustrates an exemplary embodiment of a height associated with cross-beam notches 24 relative to the height of cross-beam portions 22. In this embodiment, cross-beam notches 24 do not extend to bottom portion 18, but rather terminates a short distance above bottom portion 18. That is, in the embodiment shown in FIG. 2, the bottom portion of cross-beam portion 22 is substantially continuous. In other embodiments, the height of cross-beam notch 24 may be increased or decreased as desired, and may be extended to bottom portion 18 such that cross-beam portion 22 is effectively bisected by cross-beam notch 24.

In an exemplary embodiment of carrier tape 10, one of the goals in generating cross-beam notches 24 is to prevent the generation of repeating patterns in the location of cross-beam notches 24. The generation of repeating patterns in non-nesting features results in the possibility of non-nesting features (such as cross-beam notches 24) becoming aligned with one another in successive wraps of carrier tape 10 onto a reel. Alignment of non-nesting features such as cross-beam notches may result in the nesting of one non-nesting feature into another non-nesting feature, thereby negating the benefits of the non-nesting features. Therefore, in an exemplary embodiment the location of cross-beam notches 24 is selectively varied. This may include selectively controlling one or more of the attributes discussed above, such as varying the location of cross-beam notches 24 along the length of cross-beam portions 22, varying which cross-beam portions 22 receive cross-beam notches 24, varying the length of cross-beam notches 24, or variations to combinations of these three attributes. In particular, in an exemplary embodiment the presence of repeating patterns is reduced by relating the number of similarly-shaped pockets included in a group with a single cross-beam notch 24 to a prime number. In this way, repeating patterns in the location of cross-beam notches 24 is reduced, and the likelihood of cross-beam notches 24 becoming aligned with one another in successive wraps of carrier tape 10 onto a reel is reduced.

In addition, in the embodiment shown in FIGS. 1 and 2, carrier tape 10 includes a conventional series of equally spaced and sized drive sprocket openings 26 along one edge of strip-like portion 12 which will receive the teeth of a drive sprocket that allows carrier tape 10 to be driven through automated equipment. In addition, in the embodiment shown in FIG. 1, carrier tape 10 includes component sensing openings 28 spaced generally around the center of bottom portion 18. This opening may be used by automated equipment to sense the presence of components within similarly-shaped pocket portions 16.

Figure 3:
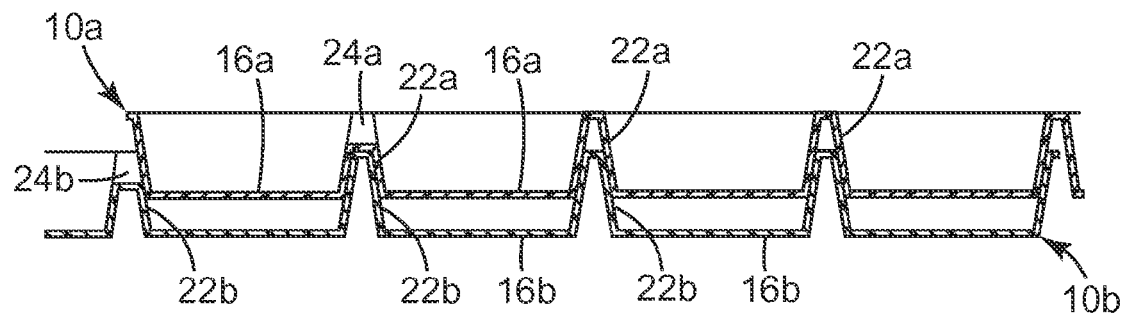
FIG. 3 is a cross-sectional view along line 3-3 of the exemplary embodiment of the carrier tape shown in FIG. 2 wound adjacent to a second portion of the carrier tape to illustrate the anti-nest feature of the carrier tape.

Portion 10a of FIG. 3 illustrates a cross-sectional view of carrier tape 10 taken along cross-section 3-3 that illustrates the effectiveness of cross-beam notches 24. In this embodiment, carrier tape 10 is wrapped around a reel (not shown) such that carrier tape 10 includes a first wrapped portion (represented by carrier tape portion 10a) and a second wrapped portion (represented by carrier tape portion 10b). As shown in FIG. 3, carrier tape portion 10b is prevented from nesting (i.e., engaging fully within carrier tape portion 10a) by cross-beam notch 24a. That is, cross-beam notch 24a acts as a stopper that prevents cross-beam portion 22b from fully engaging within cross-beam portion 22a. The result is that carrier tape portion 10b is prevented from nesting within carrier tape portion 10a, as illustrated by the small gap between cross-beam portions 22a and cross-beam portions 22b.

Figure 4:
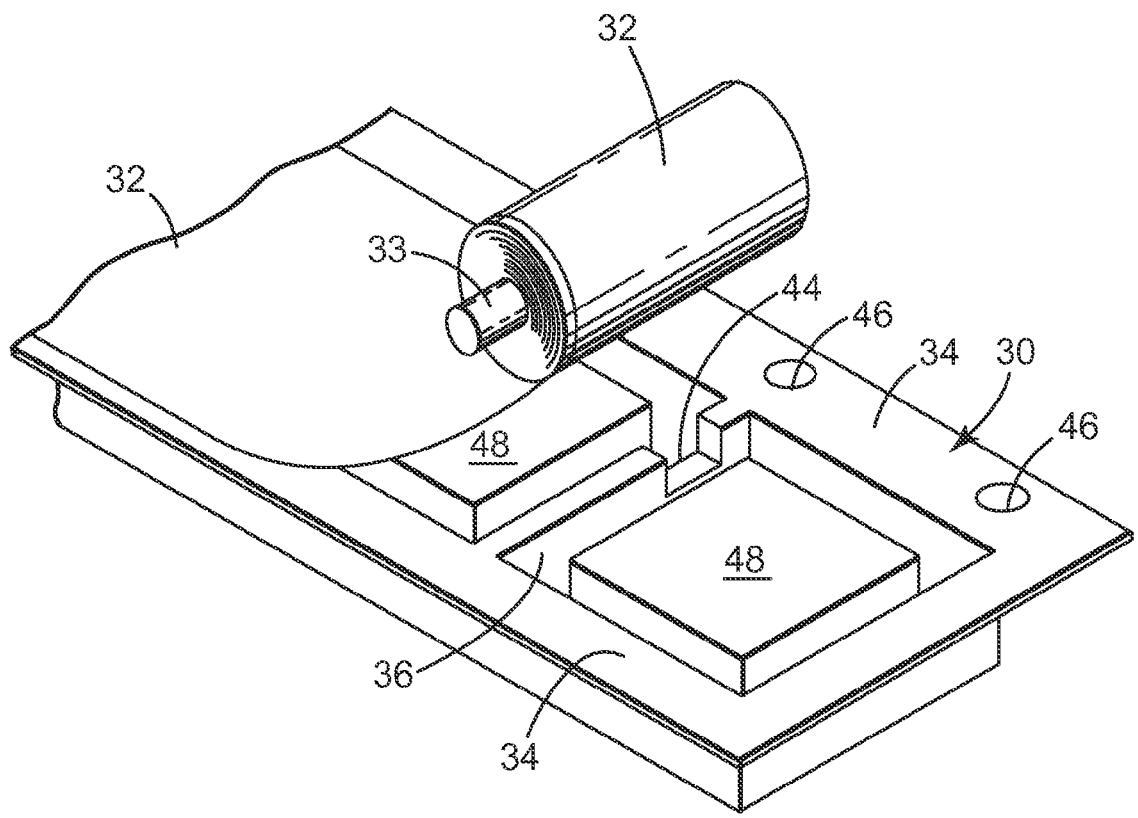
FIG. 4 is a perspective view of an exemplary embodiment of a carrier tape with a cover tape adhered to a top surface of the carrier tape.

FIG. 4 illustrates an exemplary embodiment of carrier tape 30 in which cover tape layer 32 is unwound from spool 33 and adhered to a top surface of carrier tape 30. In the embodiment shown in FIG. 4, carrier tape 30 includes top surface 34, a plurality of similarly-shaped pockets 36, side-wall portions 40, cross-beam portions 42, cross-beam notch 44, and drive-sprocket openings 46. Components 48 have been placed within each pocket 36.

Having placed each component 48 in pockets 36, cover tape layer 32 is adhered to top surface 34 of carrier tape 30. Cover tape layer 32, which is applied to carrier tape 30 prior to transporting carrier tape 30, provides a protective layer to components contained within carrier tape 30. In one embodiment, cover tape layer 32 may include a pressure sensitive material at least along its outer edges that adheres to top surface 34 of carrier tape 30 by applying a force to the outer edges of cover tape layer 32 and top surface 34. In another embodiment, cover tape layer 32 includes a heat activated material at least along its outer edges, wherein subsequent to placing cover tape layer 32 along top surface 34, heat is applied to the outer edges of cover tape layer 32 and carrier tape 30 thereby adhering cover tape layer 32 to top surface 34 of carrier tape 30.

In the exemplary embodiment shown in FIG. 4, in which the top surfaces of cross-beam portions 42 are equal in height to top surface 34 of carrier tape 30, cover tape layer 32 may also be adhered to the top surface of cross-beam portions 42 (although not in those regions in which cross-beam portion 42 contains notch 44). In other embodiments, cover tape layer 32 may only be adhered to top surface 34 of carrier tape 30, and not to the top surface of cross-beam portions 42. In either of these embodiments, the placement of cross-beam notches 44 along a length of cross-beam portions 42 does not adversely affect the ability to adhere cover tape layer 32 to carrier tape 30.

Although the present invention has been described with reference to preferred embodiments, workers skilled in the art will recognize that changes may be made in form and detail without departing from the spirit and scope of the invention.

The invention claimed is:

1. A carrier tape comprising a strip like portion defining a top surface of the tape, and wall portions defining a plurality of substantially similarly shaped pockets spaced along the carrier tape and opening through the top surface, the wall portions of one or more of the substantially similarly shaped pockets comprising:
   a bottom wall portion;
   first wall portions extending from the bottom wall portion to the top surface of the carrier tape;
   a first cross-beam wall portion extending from the bottom wall portion and located between adjacent pockets on the carrier tape; and
   a second cross-beam wall portion opposite the first cross-beam wall portion extending from the bottom wall portion and located between selected adjacent pockets on the carrier tape, wherein the second cross-beam wall portion has a notched opening formed at a selected location along a length of the second cross-beam wall portion;

wherein multiple pockets include the second cross-beam wall portions, each including a notched opening located at different locations along the length of the respective second cross-beam wall portions.

2. The carrier tape of claim 1, wherein the width of the first cross-beam wall portion and the width of the second cross-beam wall portion are approximately equal.

3. The carrier tape of claim 1, wherein sets of three or more successive pockets formed on the carrier tape include a substantially similarly-shaped pocket that includes the second cross-beam wall portion located between two of the adjacent pockets and having a notched opening formed at a selected location along the length of the second cross-beam wall portion.

4. The carrier tape of claim 1, wherein the number of the substantially similarly-shaped pockets included in a set that has at least one second cross-beam wall portion having a notched opening formed at a selected location along the length of the second cross-beam wall portion is a prime number.

5. The carrier tape of claim 1, wherein a length of the notched opening is less than half of the length of the second cross-beam wall portion.

6. The carrier tape of claim 1, wherein a height of the notched opening is less than a height of the second cross-beam wall portion such that a lower portion of the second cross-beam wall portion adjacent to the bottom wall portion is substantially continuous.

7. The carrier tape of claim 1, wherein a height of the first cross-beam wall portions and the second cross-beam wall portions are substantially equal to a height associated with the top surface of the carrier tape.

8. The carrier tape of claim 1, further including:
 a cover tape adhered to at least a portion of the top surface of the carrier tape.

9. A carrier tape comprising a strip like portion defining a top surface of the carrier tape, the carrier tape comprising:
 a number of substantially similarly-shaped pockets defined by openings in the top surface of the carrier tape, one or more of the substantially similarly-shaped pockets comprising:
 a bottom wall portion;
 first wall portions extending from the bottom wall portions to the top surface of the carrier tape;
 a first cross-beam wall portion extending from the bottom wall portions and located between adjacent pockets on the carrier tape; and
 a second cross-beam wall portion extending from the bottom wall portion and located between selected adjacent pockets on the carrier tape, wherein a top portion of each second cross-beam wall portion has a notched opening formed at a selected location along a length of the second cross-beam wall portion;
 wherein multiple pockets include the second cross-beam wall portions, each including a notched opening located at different locations along the length of the respective second cross-beam wall portions; and
 a cover tape adhered to at least a portion of the top surface of the carrier tape.

10. The carrier tape of claim 9, wherein a height of the first cross-beam wall portions and the second cross-beam wall portions are substantially equal to a height associated with the top surface of the carrier tape.

11. The carrier tape of claim 10, wherein the cover tape is adhered to one or more of a top surface of the first cross-beam wall portion and a non-notched top surface of the second cross-beam wall portion.

12. The carrier tape of claim 9, wherein the cover tape is a pressure sensitive cover tape or a heat-activated cover tape.

13. The carrier tape of claim 9, wherein sets of three or more successive pockets formed in the carrier tape include a second cross-beam wall portion located between two of the adjacent pockets.

14. The carrier tape of claim 9, wherein the height of the notched opening is less than a height of the second cross-beam wall portion such that a portion of the second cross-beam wall portion adjacent the bottom wall portion is substantially continuous.

\* \* \* \* \*